(12) United States Patent
Kwong (10) Patent No.: US 9,444,075 B2
(45) Date of Patent: Sep. 13, 2016

(54) EMISSIVE DISPLAY WITH PHOTO-SWITCHABLE POLARIZATION

(71) Applicant: Universal Display Corporation, Ewing, NJ (US)

(72) Inventor: Raymond Kwong, Fo Tan (HK)

(73) Assignee: Universal Display Corporation, Ewing, NJ (US)

( * ) Notice: Subject to any disclaimer, the term of this patent is extended or adjusted under 35 U.S.C. 154(b) by 0 days.

(21) Appl. No.: 14/554,286

(22) Filed: Nov. 26, 2014

(65) Prior Publication Data

US 2016/0149166 A1 May 26, 2016

(51) Int. Cl.
*H01L 51/52* (2006.01)
*H01L 27/32* (2006.01)
*H01L 51/00* (2006.01)

(52) U.S. Cl.
CPC ....... *H01L 51/5293* (2013.01); *H01L 27/3241* (2013.01); *H01L 51/5281* (2013.01); *H01L 51/005* (2013.01)

(58) Field of Classification Search
CPC .......... H01L 51/005; H01L 51/0052
See application file for complete search history.

(56) References Cited

U.S. PATENT DOCUMENTS

| | | | |
|---|---|---|---|
| 4,769,292 A | 9/1988 | Tang et al. | |
| 5,015,072 A | 5/1991 | Howell | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |

(Continued)

FOREIGN PATENT DOCUMENTS

| EP | 0650955 | 5/1995 |
|---|---|---|
| EP | 1725079 | 11/2006 |

(Continued)

OTHER PUBLICATIONS

Nedelchev, L. et al., "Photoinduced macroscopic chiral structures in a series of azobenzene copolyester" Appl. Phys. B 75, 671-676 (2002).

(Continued)

*Primary Examiner* — Mohammad Islam
*Assistant Examiner* — Ankush Singal
(74) *Attorney, Agent, or Firm* — Duane Morris LLP (57) ABSTRACT

Novel emissive display module and an emissive display assembly are disclosed. The emissive display module and the emissive display assembly incorporate a photo-switchable polarizer that is switchable between an active, polarizing, state and an inactive, non-polarizing, state depending on the predetermined level of intensity of UV light in the ambient light and enhance the viewable quality of the emissive display by minimizing or eliminating UV light reflection on the emissive display.

9 Claims, 3 Drawing Sheets

(56) References Cited

U.S. PATENT DOCUMENTS

| | | |
|---|---|---|
| 6,549,335 B1 | 4/2003 | Trapani et al. |
| 6,687,266 B1 | 2/2004 | Ma et al. |
| 6,835,469 B2 | 12/2004 | Kwong et al. |
| 6,861,788 B2 | 3/2005 | Li et al. |
| 6,921,915 B2 | 7/2005 | Takiguchi et al. |
| 6,999,220 B2 | 2/2006 | Kosa et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,465,414 B2 | 12/2008 | Knox et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0164921 A1 | 9/2003 | Uesaka et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0069985 A1 | 4/2004 | Cok |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2004/0189196 A1* | 9/2004 | Cok ............... 313/512 |
| 2005/0025993 A1 | 2/2005 | Thompson et al. |
| 2005/0112407 A1 | 5/2005 | Ogasawara et al. |
| 2005/0151152 A1* | 7/2005 | Miller et al. ............ 257/103 |
| 2005/0194896 A1* | 9/2005 | Sugita et al. ............ 313/506 |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0064321 A1* | 3/2007 | Hikmet et al. ............ 359/838 |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2013/0314647 A1 | 11/2013 | Yim et al. |
| 2014/0203248 A1 | 7/2014 | Zhou et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Nikolova, L. et al., "Photoinduced circular anisotropy in side-chain azobenzene polyesters," Optical Materials 8 (1997) 255-258.

Nikolova, L. et al., "Self-induced light polarization rotation in azobenzene-containing polymers," Applied Physics Letters 77, 657 (2000); doi: 10.1063/1.127076.

Pagès, S. et al., "Photoinduced linear and/or circular birefringences from light propagation through amorphous or smectic azopolymer films," Appl. Phys. B 75, 541-548 (2002).

Sumimura, H. et al., "Photoinduced Chirality in an Azobenzene Amorphous Copolymer Bearing Large Birefringent Moiety," Japanese Journal of Applied Physics, vol. 45, No. 1B, 2006, pp. 451-455.

Todorov, T. et al., "High-Sensitivity Material With Reversible Photo-Induced Anisotropy," Optics Communications, vol. 47, No. 2, Aug. 15, 1983, 123-126.

Todorov, T. et al., "Polarization holography. 1: A new high-efficiency organic material with reversible photoinduced birefringence," Applied Optics, vol. 23, No. 23, Dec. 1, 1984, 4309-4312.

Wu, Y. et al., "Photoinduced Chirality in Thin Films of Achiral Polymer Liquid Crystals Containing Azobenzene Chromophores," Macromolecules 2004, 37, 6801-6805.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

(56) References Cited

OTHER PUBLICATIONS

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).

Huang, Wei-Sheng et al., "Highly Phosphorescent Bis-Cyclometalated Iridium Complexes Containing Benzoimidazole-Based Ligands," Chem. Mater, 16(12):2480-2488 (2004).

Hung, L.S. et al., "Anode Modification in Organic Light-Emitting Diodes by Low-Frequency Plasma Polymerization of CHF3," Appl. Phys. Lett, 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett, 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

Formula 1

Formula 2

FIG. 5

EMISSIVE DISPLAY WITH PHOTO-SWITCHABLE POLARIZATION

FIELD

Aspects of the present disclosure relate generally to displays and more particularly to emissive displays such as organic light emitting diode (OLED) displays.

BACKGROUND

With the proliferation of electronic devices in modern society, technologies for displaying information to people have become more important than ever. Advances in display technology from bulky cathode ray tube (CRT) displays to liquid crystal displays (LCDs), light emitting diode (LED) displays and other displays have fueled the popularity and ubiquity of displays in the marketplace. Emissive displays, such as organic light emitting diode (OLED) displays, have become increasingly popular in recent years as they have many advantageous attributes such as relatively low weight, low cost, and low energy consumption compared to other types of displays. Emissive displays are increasingly found in mobile electronic devices such as notebook computers, tablet computers, smartphones, cameras, etc., and are increasingly being used in outdoor environments. The outdoor viewing scenario, however, presents increased unpredictability in terms of lighting conditions and increased range of possible ambient light conditions. These factors associated with outdoor use, particularly regarding strong ambient lighting, are particularly challenging for the emissive displays because of ambient light reflections on the reflective layers in the displays.

In order to improve their viewability, emissive displays often employ circular polarizers to reduce ambient light reflection by the reflective layers in the displays, particularly in bright ambient light conditions. However, circular polarizers reduce the light output from the emissive display by at least 50% because of the circular polarizer's handedness. When there is little or no ambient light, the circular polarizer reduces the emissive display's own light emission and reduce the brightness of the emissive display.

SUMMARY

In some embodiments of the present disclosure, an emissive display module includes a substrate, an array of light emissive elements provided over the substrate, and a photo-switchable polarizer provided over the array of light emissive elements. The photo-switchable polarizer is switchable between an active state and an inactive state depending on the level of intensity of UV light in ambient light of the emissive display module.

In some embodiments, an emissive display assembly includes an emissive display panel having a viewing surface, and a photo-switchable polarizer located in front of the viewing surface. The photo-switchable polarizer is switchable between an active state and an inactive state depending on the level of intensity of UV light in ambient light of the emissive display assembly.

BRIEF DESCRIPTION OF THE DRAWINGS

The following will be apparent from elements of the figures, which are provided for illustrative purposes and are not necessarily to scale.

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "vertically," "downwardly," "upwardly," etc.) should be construed to refer to the orientation as then described or as shown in the drawing under discussion. These relative terms are for convenience of description and do not require that the apparatus be constructed or operated in a particular orientation.

Various embodiments of the present disclosure address the above-described challenges associated with emissive displays. By providing a polarizer to make an emissive display easier to view in bright ambient light settings (e.g., outdoor lighting environment) and enabling the polarization functionality to be toggled on or off depending on ambient lighting conditions, various embodiments yield an efficient display solution that performs well in various lighting scenarios.

Figure 1:
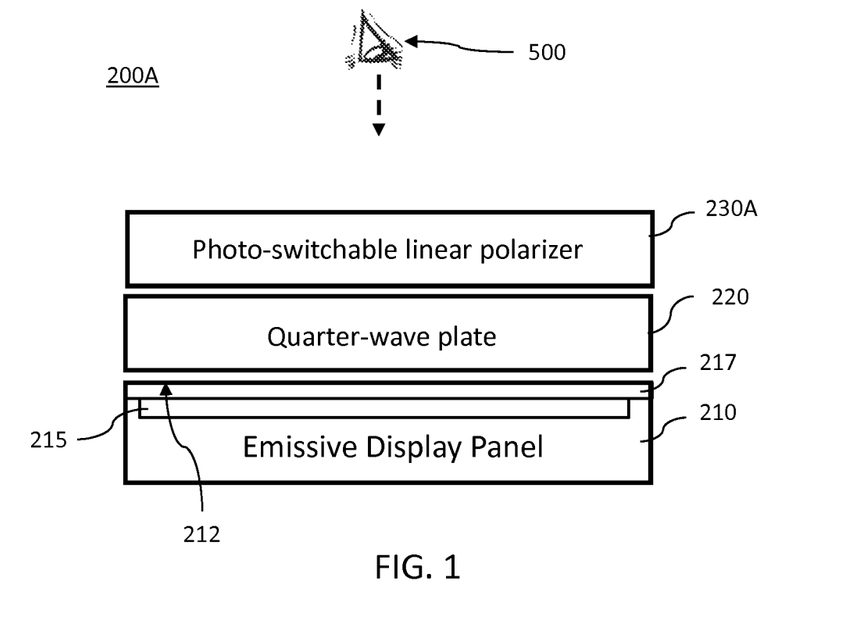
FIG. 1 is a cross-sectional view of an emissive display assembly in accordance with some embodiments of the present disclosure.

FIG. 1 is a simplified schematic cross-sectional view of an emissive display assembly 200A according to an embodiment. The emissive display assembly 200A comprises an emissive display panel 210 having a viewing surface 212; and a reversibly photo-switchable linear polarizer 230A located in front of the viewing surface 212. The reversibly photo-switchable linear polarizer 230A is switchable between an active state and an inactive state depending on the level of intensity of ultraviolet (UV) light in the ambient light of the emissive display assembly 200A. When the reversibly photo-switchable linear polarizer 230A is in the active state, the photo-switchable polarizer linearly polarizes the light passing therethrough. On the other hand, when the reversibly photo-switchable linear polarizer 230A is in the inactive state, the photo-switchable polarizer allows light to pass through without polarizing the light.

Figure 3:
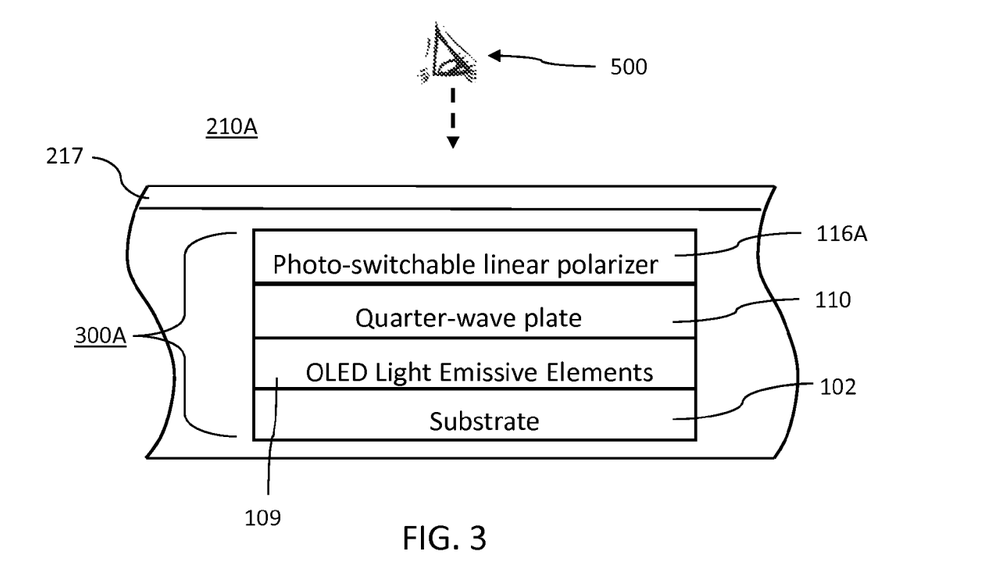
FIG. 3 is a schematic cross-sectional illustration of the emissive display module according to an embodiment.
Figure 4:
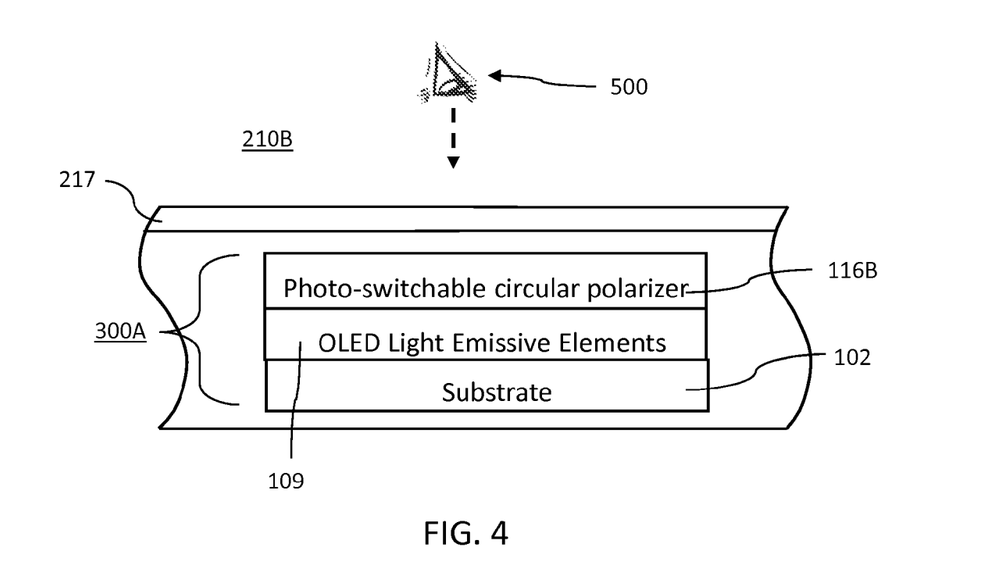
FIG. 4 is a schematic cross-sectional illustration of the emissive display module according to another embodiment.

The term "front" as used herein refers to the side of the emissive display panel 210 or the emissive display module 300A, 300B facing the viewer 500.

In this embodiment, the emissive display assembly 200A further comprises a quarter-wave plate 220 located between the photo-switchable linear polarizer 230A and the emissive display panel 210. A quarter-wave plate 220 converts linearly polarized light into circularly polarized light and vice versa.

Figure 2:
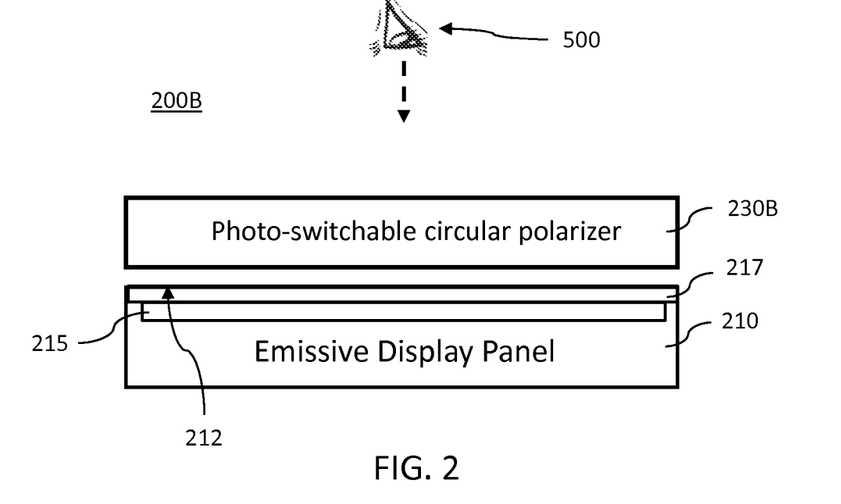
FIG. 2 is a cross-sectional view of an emissive display assembly in accordance with some other embodiments.

Referring to FIG. 2, in another embodiment, an emissive display assembly 200B comprises an emissive display panel 210 and a reversibly photo-switchable circular polarizer 230B provided in front of the viewing surface 212. The photo-switchable circular polarizer 230B is switchable between an active state (polarizing state) and an inactive state (non-polarizing state) depending on the level of intensity of UV light in the ambient light of the emissive display assembly 200B. When in its active state, the photo-switchable circular polarizer 230B circularly polarizes the light passing therethrough.

In the various embodiments described herein, the emissive display panel 210 includes an array of OLED light emissive elements 215 that form the images seen by the viewer 500 through the viewing surface 212. The viewing surface 212 can be formed by a transparent protective layer 217.

Referring to FIG. 3, according to another embodiment, an emissive display panel 210A comprising an emissive display module 300A is disclosed. The emissive display module 300A comprises a substrate 102, an array of OLED light emissive elements 109 provided on the substrate 102, and a reversibly photo-switchable linear polarizer layer 116A provided over the array of OLED light emissive elements 109. Similar to the reversibly photo-switchable polarizers 230A, 230B, the reversibly photo-switchable linear polarizer layer 116A is switchable between an active polarizing state and an inactive non-polarizing state depending on the level of intensity of UV light in the ambient light of the emissive display module 300A.

Because the photo-switchable polarizer layer 116A is a linear polarizer, the emissive display module 300A further comprises a quarter-wave plate 110 located between the photo-switchable linear polarizer layer 116A and the array of OLED light emissive elements 109. The emissive display panel 210A can include a transparent protective layer 217 for protecting the emissive display module 300A as shown in FIG. 3.

Referring to FIG. 4, according to another embodiment, an emissive display panel 210B comprising an emissive display module 300B is disclosed. The emissive display module 300B comprises a substrate 102, an array of OLED light emissive elements 109 provided on the substrate 102, and a reversibly photo-switchable circular polarizer layer 116B provided over the array of OLED light emissive elements 109. The reversibly photo-switchable circular polarizer layer 116B is switchable between an active polarizing state and an inactive non-polarizing state depending on the level of intensity of UV light in the ambient light of the emissive display module 300B. The emissive display panel 210B can include a transparent protective layer 217 for protecting the emissive display module 300B as shown in FIG. 4.

In various embodiments described herein, the substrate 102 may be formed from any one or more of various materials, including silicon, glass, plastic, ceramics, and metal suitable for OLED substrates. Although the details of various sub-components of the array of OLED light emissive elements 215 and 109 are not shown or described in detail, one of ordinary skill in the art would readily understand that the OLED light emissive elements 215 and 109 would include such structures and components as the OLED pixels, electrodes for delivering the driving current to the OLED pixel arrays, power supplies, etc. for the array of OLED light emissive elements 215, 109 to form images viewed by the viewer 500.

In various embodiments described herein, the reversibly photo-switchable polarizer (any of 230A, 230B, 116A, 116B) comprises one or more of reversibly photo-switchable polarizing material(s) that is/are in an active polarizing (ON) state when the level of intensity of the UV light in the ambient light is greater than or equal to a predetermined level and in an inactive non-polarizing (OFF) state when the level of intensity of the UV light in the ambient light is less than the predetermined level. For example, reversibly photo-switchable polarizing material can be selected so that the predetermined level of the intensity of the UV light in the ambient light that would switch the photo-switchable polarizing material between the ON/OFF states is 0.1 W/m$^2$ (at 365 nm). In such example, the photo-switchable polarizing material will switch to its ON state when the intensity of the UV light in the ambient light is ≥0.1 W/m$^2$ (at 365 nm) and switch to its OFF state when the UV light intensity in the ambient light is <0.1 W/m2 (at 365 nm).

Activation and deactivation of the photo-switchable polarizing material(s) can be effected by molecular rearrangement and alignment of the photo-switchable polarizing materials Linear, rod-like materials such as conjugated azobenzene type compounds would induce linear polarization. Chiral materials such as twisted aromatics (e.g., hexahelicene) would induce circular polarization. In some embodiments, the degree of polarization is controllable because the level of molecular arrangement in the photo-switchable polarizer depends on the amount of UV light in the ambient light. The aligned state and the random state are in equilibrium. More materials are in the aligned (polarization) state when there is more UV light. For example, at UV irradiance of 0.1 W/m$^2$ (at 365 nm), ≥90% of the materials are in the aligned state, and at 0.01 W/m$^2$ (at 365 nm), ≤10% of the materials are in the aligned state.

In the active polarizing state, ambient light reflection in the emissive display assembly 200A/200B or emissive display module 300A/300B is reduced, making the displayed light output easier for viewer 500 to view in bright outdoor conditions, for example. In some embodiments, absorption by the reversibly photo-switchable polarizing material(s) occurs at wavelengths of 420 nm or higher. This can ensure minimal absorption of OLED emitted light in some embodiments, leading to unblocked, full utilization of the OLED emission

In one embodiment, the device comprising the display and the photo-switchable polarizer is equipped with a sensor which detects the UV intensity of the UV irradiance level in the ambient light and adjusts the display brightness accordingly. For example, when the sensor detects a UV irradiance of ≥0.1 W/m$^2$ (at 365 nm), the display is adjusted to a high brightness mode, e.g., at an intrinsic OLED brightness of 1000 cd/m$^2$ and extrinsic brightness of 500 cd/m$^2$, (assuming the polarizer blocks 50% of the light) as the photo-switchable polarizer will be at the ON state. When the sensor detects a UV irradiance of ≤0.01 W/m$^2$ (at 365 nm), the display is adjusted to a low brightness mode, e.g., at an intrinsic OLED brightness of 200 cd/m$^2$ and extrinsic brightness of 200 cd/m$^2$ as the photo-switchable polarizer is at the OFF state. On the other hand, if a regular, always "on" polarizer is used, even when the UV irradiance is ≤0.01 W/m$^2$ (at 365 nm), in order to reach an external brightness of 200 cd/m$^2$, the intrinsic brightness needs to be at 400 cd/m$^2$. Energy saving can be achieved.

In the inactive non-polarizing state, the reversibly photo-switchable polarizer (any of 230A, 230B, 116A, 116B) is transparent to the emission of light (does not significantly absorb emitted light). Thus, in sufficiently dim indoor conditions (for example), the polarization functionality is switched off Thus, in various embodiments polarization is only activated when needed.

Figure 5:
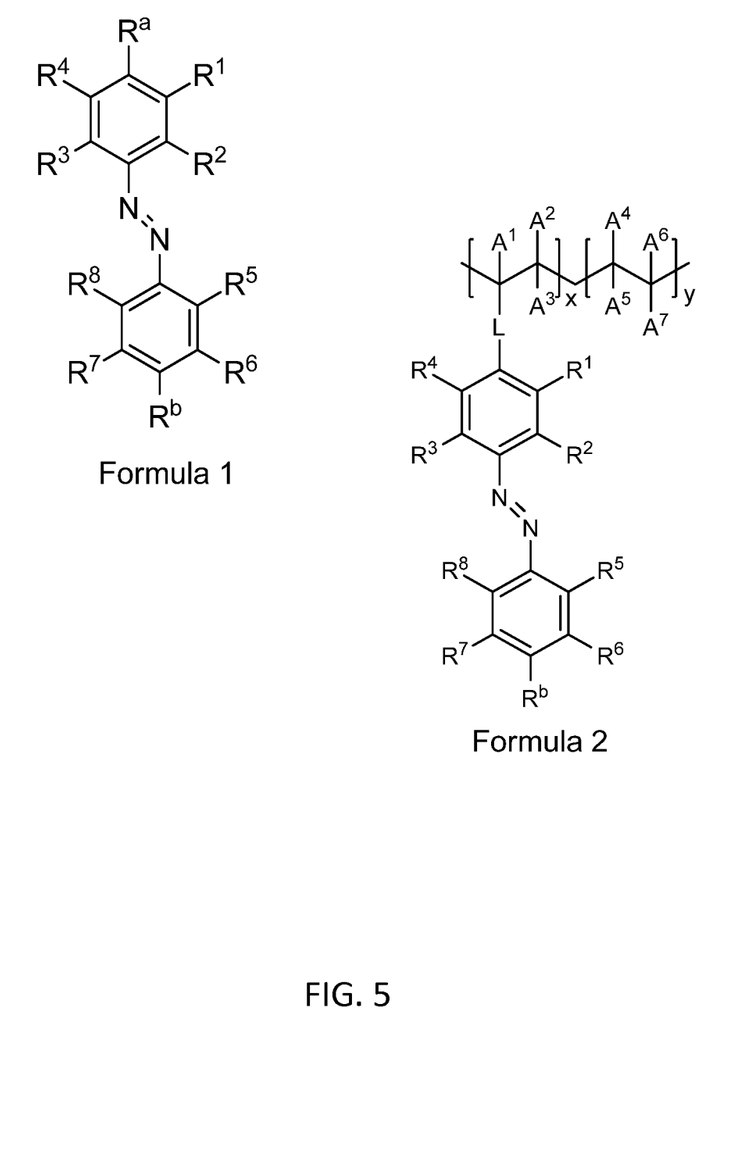
FIG. 5 shows the chemical structures according to Formula 1 and Formula 2 that are examples of the reversibly photo-switchable polarizing materials disclosed herein.

The reversibly photo-switchable polarizing material(s) used in the photo-switchable polarizer in various embodiments may include any material that exhibits variable polarization based on ambient UV light. Such materials are known for use in, for example, photochromic eyeglasses that darken upon exposure to specific types of light. By way of non-limiting examples, such reversibly photo-switchable materials include one or more azobenzene compounds doped in a polymer material such as poly-methylmethacrylate and poly-vinyl polymer may be used. An example of such an azobenzene compound has a structure according to Formula 1 shown below Formula 1

In another example, the reversible photo-switchable material can be one or more polymers with azobenzene derivative pendant groups such as compounds having the structure according to Formula 2 shown below may also be used.

Formula 2

In Formula 1 and Formula 2 shown in FIG. 5, $R^a$, $R^b$, $R^1$-$R^8$ and $A^1$-$A^7$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof L is a linker; and x is an integer ≥1 and y is integer ≥0.

The previous description of the embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. An emissive display module comprising:
   a substrate;
   an array of OLED light emissive elements provided over the substrate; and
   a photo-switchable polarizer provided over the array of OLED light emissive elements,
   wherein the photo-switchable polarizer is switchable between an active state and an inactive state depending on a level of intensity of UV light in ambient light of the emissive display module.

2. The emissive display module of claim 1, wherein the photo-switchable polarizer is in the active state when the level of intensity of the UV light in the ambient light is greater than or equal to a predetermined level and the photo-switchable polarizer is in the inactive state when the level of intensity of the UV light in the ambient light is less than the predetermined level.

3. The emissive display module of claim 1, wherein the photo-switchable polarizer is a circular polarizer.

4. The emissive display module of claim 3, wherein the photo-switchable polarizer is in the active state when the level of intensity of the UV light in the ambient light is greater than or equal to a predetermined level and the photo-switchable polarizer is in the inactive state when the level of intensity of the UV light in the ambient light is less than the predetermined level.

5. The emissive display module of claim 1, wherein the photo-switchable polarizer comprises one or more azobenzene compounds doped in a polymer material selected from poly-methylmethacrylate or poly-vinyl polymer.

6. The emissive display module of claim 5, wherein the azobenzene compound has a structure according to Formula 1:

Formula 1 wherein $R^a$, $R^b$, and $R^1$-$R^8$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

7. The emissive display module of claim 1, wherein the photo-switchable polarizer comprises one or more polymer compounds with azobenzene derivative pendant groups, the one or more polymer compounds having a structure according to Formula 2:

Formula 2 wherein $R^a$, $R^b$, $R^1$-$R^8$ and $A^1$-$A^7$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, arylamino, diarylamino, carbazolyl, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

L is a linker; and x is an integer $\geq 1$ and y is integer $\geq 0$.

8. The emissive display module of claim 1, wherein the photo-switchable polarizer is a linear polarizer, the emissive display module further comprising a quarter wave plate located between the photo-switchable polarizer and the array of OLED light emissive elements.

9. The emissive display module of claim 8, wherein the photo-switchable polarizer is configured to be in the active state when the level of intensity of the UV light in the ambient light is greater than or equal to a predetermined level and the photo-switchable polarizer is configured to be in the inactive state when the level of intensity of the UV light in the ambient light is less than the predetermined level.

* * * * *

UNITED STATES PATENT AND TRADEMARK OFFICE
CERTIFICATE OF CORRECTION

PATENT NO.      : 9,444,075 B2
APPLICATION NO. : 14/554286
DATED           : September 13, 2016
INVENTOR(S)     : Raymond Kwong

Page 1 of 2

It is certified that error appears in the above-identified patent and that said Letters Patent is hereby corrected as shown below:

In the Specification

In Column 1, at Line 9 insert:
-- PARTIES TO A JOINT RESEARCH AGREEMENT
The claimed invention was made by, on behalf of, and/or in connection with one or more of the following parties to a joint university corporation research agreement: The Regents of the University of Michigan, Princeton University, University of Southern California, and Universal Display Corporation. The agreement was in effect on and before the date the claimed invention was made, and the claimed invention was made as a result of activities undertaken within the scope of the agreement. --

In Column 5, Lines 33-53 delete:

"" and insert

Signed and Sealed this
Thirty-first Day of October, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,444,075 B2

Formula 2

-- "                    " --

In the Claims

In Column 7, Lines 6-25 delete:

" and insert --

Formula 2

--